United States Patent
Petroff, II et al.

(10) Patent No.: US 11,952,360 B2
(45) Date of Patent: Apr. 9, 2024

(54) DIBENZOTHIOPHENE COMPOUNDS

(71) Applicant: Saint Louis University, St. Louis, MO (US)

(72) Inventors: John T. Petroff, II, St. Louis, MO (US); Ryan D. McCulla, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 450 days.

(21) Appl. No.: 16/795,708

(22) Filed: Feb. 20, 2020

(65) Prior Publication Data

US 2020/0262808 A1    Aug. 20, 2020

Related U.S. Application Data

(60) Provisional application No. 62/807,973, filed on Feb. 20, 2019.

(51) Int. Cl.
  *C07D 333/76*   (2006.01)
  *B01J 23/06*    (2006.01)
  *G01N 33/58*    (2006.01)

(52) U.S. Cl.
  CPC ............ *C07D 333/76* (2013.01); *B01J 23/06* (2013.01); *G01N 33/582* (2013.01)

(58) Field of Classification Search
  CPC .................................................. C07D 333/76
  See application file for complete search history.

(56) References Cited

U.S. PATENT DOCUMENTS

2018/0319765 A1    11/2018    Petroff et al.

OTHER PUBLICATIONS

Dygos, et al. Journal of Medicianl Chemistry, 1977, 20, 1705-1708.*
Bourdillon, M. T., et al., "Oxidation of Plasmalogen, Low-Density Lipoprotein, and RAW 264.7 Cells by Photoactivatable Atomic Oxygen Precursors," 2014, Photochemistry and Photobiology, 90/2:386-393, 18 pages.
Bucher, G., et al., "Laser Flash Photolysis of Pyridine N-Oxide: Kinetic Studies of Atomic Oxygen [O(3P)] in Solution," 1994, J Phys Chem, 98:12471-12473, p. 1 only.
Cubbage, J. W., et al., "Bimolecular Photoreduction of Aromatic Sulfoxides," 2001, J Org Chem, 66:8621-8628, 8 pages.
Dias, F. B., et al., "The Roll of Local Triplet Excited States and D-A Relative Orientation in Thermally Activated Delayed Fluorescence: Photophysics and Devises," 2016, Advanced Science 2016, 3, 1600080, wileyonlinelibrary.com, 10 pages.
Dunn, K. W., et al., "A Practical Guide to Evaluating Colocalization in Biological Microscopy," 2011, Am J Cell Physiol, 300:C723-C742, 20 pages.

Gregory, D. D., et al., "Photodeoxygenation of Dibenzothiophene Sulfoxide: Evidence for a Unimolecular S-O Cleavage Mechanism," 1997, JACS. 119: 94-102, 9 pages.
Jenks, W. S., et al., "Photochemistry and Photophysics of Aromatic Sulfoxides. 1. Characterization of the Triplets at Cryogenic Temperatures," 1994, J Phys Chem, 98:2282-2289, p. 1 only.
Korang, J., et al., Photoinduced DNA Cleavage by Atomic Oxygen Precursors in Aqueous Solutions, 2013, RSC Advances, 3/30:12390-12397, Abstract only, 1 page.
Korang, J., et al., "Photodeoxygenation of Dibenzothiophene S-Oxide Derivatives in Aqueous Media," 2010, JACS, 132/12:4466-4476, Abstract only, 1 page.
Lavis, L. D, et al., "Bright Ideas for Chemical Biology," Mar. 2008, ACS Chemical Biology 3/3:142-155, 21 pages.
Liu, J., et al., Novel Spectrally Stable Saturated Blue-Light-Emitting Poly[(fluorine)-co-(dioctyldibenzothiophene-S,S-dioxide)]s, Mar. 2010, Macromol Rapid Commun, 31/5:496-501, Abstract only, 1 page.
Lucien, E., et al., "Electrophilic Oxidant Produced in the Photodeoxygenation of 1,2-Bezodiphenylene Sulfoxide," 2001, J Org Chem, 66:4576-4579, 4 pages.
McCulla, R. D., "Photochemistry and internal eliminations of organosulfur and organoselenium compounds," Iowa State University, 2005. 321 pages.
McCulla, R. D., et al., "Deoxygenation and Other Photochemical Reactions of Aromatic Selenoxides," 2004, JACS, 126:16058-16065, 8 pages.
Nag, M., et al., "Photochemistry and Photophysics of Halogen-Substituted Dibenzothiophene Oxides, " 2004, JOC, 69/24:8177-8182, 6 pages.
Omlid, S. M., et al., "Thiol Reactivity Toward Atomic Oxygen Generated During the Photodeoxygenation of Dibenzothiophene S-Oxide," 2017, JOC, 82/24:12947-12966, Abstract only, 1 page.
Petroff, II, J.T., et al., "Dibenzothiophene Sulfone Derivatives as Plasma Membrane Dyes," 2020, Photochem Photobiol, 96/1:67-73.
Petroff, II, J. T., et al., "Asymmetric Dibenzothiophene Sulfones as Fluorescent Nuclear Stains," Oct. 2018, J Org Chem, 83,/22:14063-14068. Abstract only.
Renz, M., "Fluorescence Microscopy—A Historical and Technical Perspective," 2013, Cytometry Part A 83A:767-779, 13 pages.
Rockafellow, E. M., et al., "Deoxygenation of Dibenzothiophene-S-Oxide and Dibenzoselenophene-Se-Oxide: A Comparison of Direct and Sensitized Photolysis," 2008, J Photochem Photobiol A: Chemistry 198:45-51, 7 pages.
Specht, E. A, et al., "A Critical and Comparative Review of Fluorescent Tools for Live-Cell Imaging," 2017, Annual Review of Physiology, 79:93-117, 28 pages.

(Continued)

*Primary Examiner* — Shawquia Jackson
(74) *Attorney, Agent, or Firm* — Stinson LLP

(57) ABSTRACT

The present invention generally relates to various dibenzothiophene compounds, processes for preparing these compounds, and uses of these compounds. The present invention also relates to cell imaging agents comprising one or more of the dibenzothiophene compounds and processes for imaging a cell using the compounds. The present invention further relates to methods of producing ground state atomic oxygen.

19 Claims, 5 Drawing Sheets
(2 of 5 Drawing Sheet(s) Filed in Color)

(56) References Cited

OTHER PUBLICATIONS

Stoffregen, S. A., et al., "Computational Investigation of the Photochemical Deoxygenation of Thiophene-S-Oxide and Selenophene-Se-Oxide," Feb. 2014, Photochem Photobiol Sci, 13/2:431-438.

Terai, T., et al., "Small-Molecule Fluorophores and Fluorescent Probes for Bioimaging," 2013, European Journal of Physiology 465:347-359.

Thomas, K. B., et al., "Gauging the Significance of Atomic Oxygen [O(3P)] in Sulfoxide Photochemistry. A Method for Hydrocarbon Oxidation," 2003, J Org Chem, 68:1886-1891, 6 pages.

Vos, B. W., et al., "Evidence for a Nonradical Pathway in the Photoracemization of Aryl Sulfoxides," 2002, JACS, 124:2544-2547, 4 pages.

Wan, Z., et al., "Oxenoid Reactivity Observed on the Photolysis of Certain Aromatic Sulfoxides, " 1995, JACS, 117:2667-2779, p. 1 only.

Wauchope, O. R. et al., "Photocleavage of Plasmid DNA by Dibenzothiophene S-Oxide Under Anaerobic Conditions," Feb. 2007, J Sulfur Chemistry, 28/1:11-16, 6 pages.

Wiederschain, G.Y., Book Review: "The Molecular Probes Handbook. A Guide to Fluorescent Probes and Labeling Technologies," Nov. 2011, Biochemistry (Moscow), 76/11:1276.

Zhang, M., et al., "Redox Switching of Adenosine-5'-Phosphosulfate Kinase with Photoactivatable Atomic Oxygen Precursors," Oct. 2012, JACS, 134/41:16979-16982, Abstract only, 1 page.

\* cited by examiner

DIBENZOTHIOPHENE COMPOUNDS

REFERENCE TO RELATED APPLICATIONS

This application claims benefit of U.S. provisional application Ser. No. 62/807,973, filed Feb. 20, 2019, the entire disclosure of which is incorporated herein by reference.

STATEMENT REGARDING FEDERALLY SPONSORED RESEARCH OR DEVELOPMENT

This invention was made with Government support under CHE-1255270 awarded by the National Science Foundation. The Government has certain rights in the invention.

FIELD OF THE INVENTION

The present invention generally relates to various dibenzothiophene compounds, processes for preparing these compounds, and uses of these compounds. In particular, the compounds of the present invention include various sulfone and sulfoxide analogs of various dibenzothiophene compounds. The present invention also relates to cell imaging agents comprising one or more of the dibenzothiophene compounds and processes for imaging a cell using the compounds. The present invention further relates to methods of producing ground state atomic oxygen.

BACKGROUND OF THE INVENTION

Various methods for staining tissue and cells involve the use of antibodies, fluorescent proteins, or materials that provide for fluorescent imaging. However, each method has its own set of advantages or disadvantages. For a small molecule dye, the innate limitations of a molecule's photophysics are often the cause that disallow the dye's use. This problem is described by Terai and Nagano in *Pflügers Archiv—European Journal of Physiology* 2013, 465, 347, who note the difficulty of predicting a given molecule's photophysics. Thus, there remains a need for new small molecule fluorescent molecules that have low cell toxicity and can be used as fluorescent dyes to expand the toolkit of fluorescent microscopy.

BRIEF SUMMARY OF THE INVENTION

The present invention generally relates to various dibenzothiophene compounds, processes for preparing these compounds, and uses of these compounds. Various dibenzothiophene compounds of the present invention include those having the structure of Formula (I) and salts thereof:

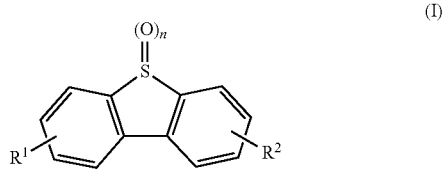
(I)

wherein
R$^1$ is hydrogen, hydoxy, substituted or unsubstituted hydrocarbyl, or substituted or unsubstituted amino;
R$^2$ is:

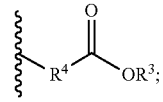

R$^3$ is hydrogen, substituted or unsubstituted alkyl, substituted or unsubstituted alkenyl, or substituted or unsubstituted alkynyl;
R$^4$ is substituted or unsubstituted alkylene, substituted or unsubstituted alkenylene, or substituted or unsubstituted alkynylene; and n is 1 or 2. The present invention also relates to various processes for preparing these compounds.

The present invention also relates to imaging agents useful for visualizing a cell. The imaging agents can comprise one or more compounds of Formula (I) (particularly where n is 2). Further, the present invention relates to processes of visualizing a cell comprising applying the imaging agent to the cell, applying a luminescent probe (e.g., light) to stimulate the emission of a luminescent signal from the imaging agent, and detecting the signal.

The present invention further relates to methods of generating ground state atomic oxygen [O($^3$P)]. These methods comprise irradiating a sulfoxide analog of formula (I) (i.e., where n is 1) with UV light to produce ground state atomic oxygen [O($^3$P)]. The sulfoxide analog can be applied to cells, tissues, or other living systems prior to irradiation.

Other objects and features will be in part apparent and in part pointed out hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
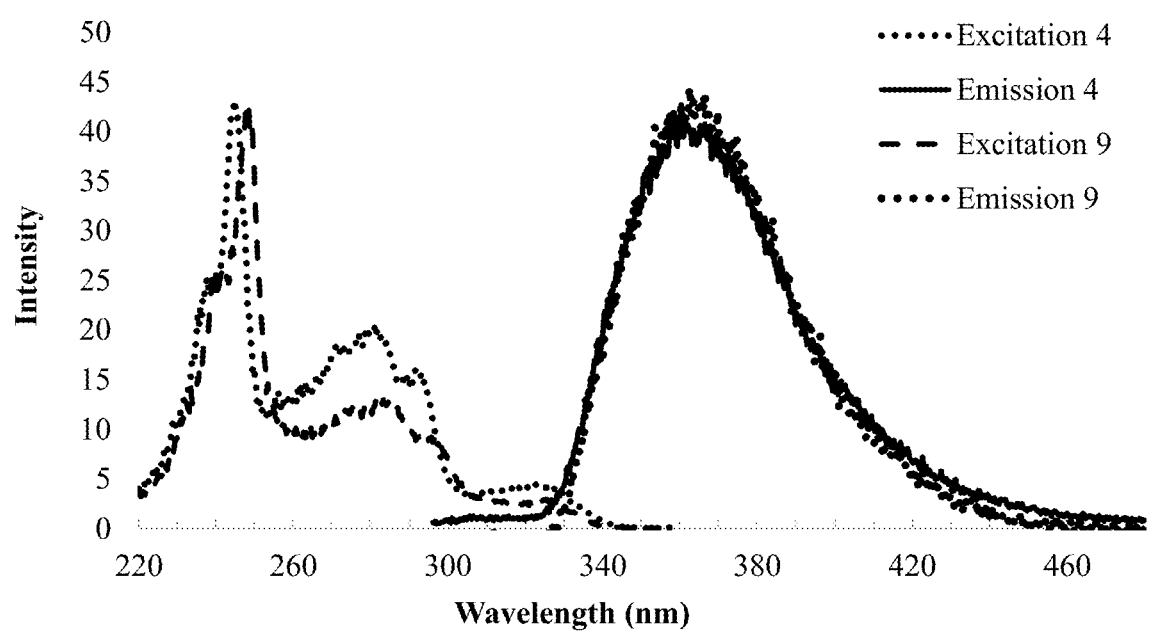
FIG. 1 presents a graph of excitation and emission scans of compounds 4 and 9.

In general, the present invention is directed to various dibenzothiophene compounds, processes for preparing these compounds, and uses of these compounds. In particular, the compounds of the present invention include various sulfone and sulfoxide analogs of various dibenzothiophene compounds. The present invention also relates to processes for using these compounds as cell imaging agents and methods of producing ground state atomic oxygen.

The functionalization of dibenzothiophenes and their fluorescent analogs dibenzothiophenes-5,5-dioxides (DBTOOs) was found to direct small molecules into specific cellular components. In an effort to localize DBTOOs in the plasma membrane, small molecules have been produced with different functional groups.

In various aspects, the present invention is directed to compounds having the structure of Formula (I) and salts thereof:

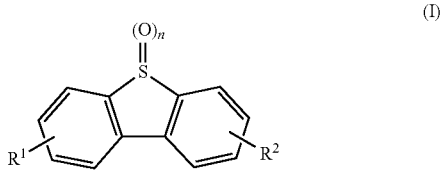

(I)

wherein
$R^1$ is hydrogen, hydoxy, substituted or unsubstituted hydrocarbyl, or substituted or unsubstituted amino;
$R^2$ is:

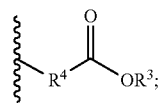

$R^3$ is hydrogen, substituted or unsubstituted alkyl, substituted or unsubstituted alkenyl, or substituted or unsubstituted alkynyl;
$R^4$ is substituted or unsubstituted alkylene, substituted or unsubstituted alkenylene, or substituted or unsubstituted alkynylene; and
n is 1 or 2.

In various embodiments, $R^1$ is hydrogen, hydroxy, substituted or unsubstituted $C_1$-$C_{20}$ alkyl, substituted or unsubstituted $C_2$-$C_{20}$ alkenyl, or substituted or unsubstituted $C_2$-$C_{20}$ alkynyl, substituted or unsubstituted $C_1$-$C_{20}$ alkoxy, substituted or unsubstituted aryl, substituted or unsubstituted heteroaryl. In some embodiments, $R^1$ is hydrogen, hydroxy, substituted or unsubstituted $C_1$-$C_{12}$ alkyl, substituted or unsubstituted $C_2$-$C_{12}$ alkenyl, or substituted or unsubstituted $C_2$-$C_{12}$ alkynyl, substituted or unsubstituted $C_1$-$C_{12}$ alkoxy, substituted or unsubstituted aryl, substituted or unsubstituted heteroaryl. In further embodiments, $R^1$ is hydrogen, hydroxy, substituted or unsubstituted $C_1$-$C_{12}$ alkyl, substituted or unsubstituted $C_2$-$C_{12}$ alkenyl, or substituted or unsubstituted $C_2$-$C_{12}$ alkynyl, substituted or unsubstituted $C_1$-$C_{12}$ alkoxy, substituted or unsubstituted aryl, substituted or unsubstituted heteroaryl. The substituted or unsubstituted heteroaryl, as referred to herein, can be a substituted or unsubstituted nitrogen-containing heteroaryl. Also, $R^1$ can be a 5- or 6-membered aromatic ring.

In various embodiments, $R^1$ is hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_1$-$C_{12}$ alkoxy, substituted or unsubstituted phenyl, substituted or unsubstituted biphenyl, substituted or unsubstituted naphthyl, or substituted or unsubstituted anthracenyl. In some embodiments, $R^1$ is phenyl, hydroxyphenyl, ethylphenyl, carboxyphenyl, naphthyl, anthracenyl, biphenyl, tolyl, cumyl, styryl, ortho-xylyl, meta-xylyl, para-xylyl, fluorophenyl, chlorophenyl, bromobenzyl, or iodobenzyl.

In various embodiments, $R^1$ is a linear or branched $C_1$-$C_{12}$ alkyl. In some embodiments, $R^1$ is a linear $C_4$-$C_{12}$ alkyl.

In some embodiments, $R^1$ is hydrogen. In other embodiments, $R^1$ is not hydrogen.

As noted above, $R^2$ is a moiety of the following structure:

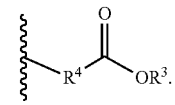

In various embodiments, $R^2$ is derived from a carboxylic acid (e.g., monocarboxylic acid) or a salt of a carboxylic acid. In some embodiments, $R^2$ is derived from a fatty acid (e.g., $C_4$-$C_{28}$ fatty acids, which can be saturated or unsaturated, and branched or unbranched) or a salt thereof.

In various embodiments, $R^3$ is hydrogen, substituted or unsubstituted $C_1$-$C_{20}$ alkyl, substituted or unsubstituted $C_2$-$C_{20}$ alkenyl, or substituted or unsubstituted $C_2$-$C_{20}$ alkynyl. In some embodiments, $R^3$ is hydrogen, substituted or unsubstituted $C_1$-$C_{12}$ alkyl, substituted or unsubstituted $C_2$-$C_{12}$ alkenyl, or substituted or unsubstituted $C_2$-$C_{12}$ alkynyl. In further embodiments, $R^3$ is hydrogen, $C_1$-$C_{12}$ alkyl, $C_2$-$C_{12}$ alkenyl, or $C_2$-$C_{12}$ alkynyl. In certain embodiments, $R^3$ is hydrogen.

In various embodiments, $R^4$ is a substituted or unsubstituted $C_1$-$C_{20}$ alkylene, substituted or unsubstituted $C_2$-$C_{20}$ alkenylene, or substituted or unsubstituted $C_2$-$C_{20}$ alkynylene. In some embodiments, $R^4$ is a substituted or unsubstituted $C_1$-$C_{12}$ alkylene, substituted or unsubstituted $C_2$-$C_{12}$ alkenylene, or substituted or unsubstituted $C_2$-$C_{12}$ alkynylene. In further embodiments $R^4$ is a $C_1$-$C_{12}$ alkylene, $C_2$-$C_{12}$ alkenylene, or $C_2$-$C_{12}$ alkynylene. In certain embodiments, $R^4$ is a $C_1$-$C_{12}$ alkylene, $C_4$-$C_{12}$ alkenylene, or $C_4$-$C_{12}$ alkynylene.

In various embodiments, $R^4$ is a linear $C_1$-$C_6$ alkylene (e.g., methylene, ethylene, propylene, butylene, etc.). In certain embodiments, $R^4$ is a linear $C_3$ alkylene (i.e., propylene).

Typically, the compounds of the present invention are asymmetrical. In other words, $R^1$ and $R^2$ are typically different substituents.

In various embodiments, n is 2. In other embodiments, n is 1.

The compounds of the present invention are typically substituted at the 2- and/or 8-position of the dibenzothiophene scaffold. In various embodiments, the compounds of the present invention have a structure of formula (II-a) or (II-b):

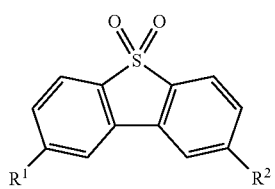

(II-a)

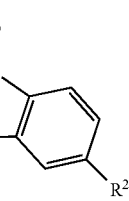

(II-b)

wherein R¹ and R² are as defined for Formula (I) above.

In various embodiments, the compound of Formula (I) or (II-a) is selected from the group consisting of:

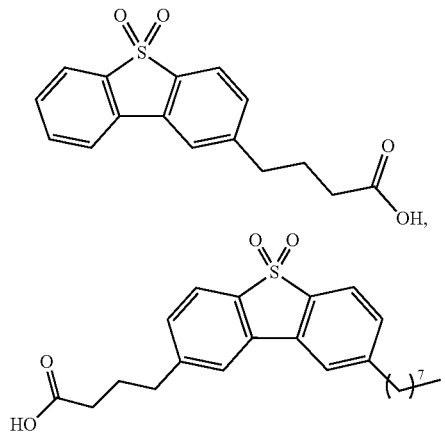

and salts thereof.

As noted, the present invention also relates to processes for preparing the compounds of Formulas (I), (II-a), and (II-b). For example, various processes for preparing these compounds use dibenzothiophene (for monosubstituted dibenzothiophene-5,5-dioxides) or a 4-bromo analog (for dimonosubstituted dibenzothiophene-5,5-dioxides) as the starting material.

The synthesis of 4-(5,5-dioxidodibenzo[b,d]thiophen-2-yl)butanoic acid (compound 4), which a monosubstituted dibenzothiophene-5,5-dioxide, is shown in Scheme 1. The synthesis involves the addition of an oxobutanoic acid to the 2-position on the dibenzothiophene (1). This is achieved using succinic anhydride in the presence of aluminum trichloride (AlCl₃) dissolved in a 2:1 solution of dichloroethane (DCE) and nitrobenzene under an inert atmosphere. Following sequential recrystallizations in 2:1 ethyl acetate and chloroform, the product 4-(dibenzo[b,d]thiophen-2-yl)-4-oxobutanoic acid (2) is isolated. The product (2) is then reduced to the butanoic acid form by zinc amalgam to form 4-(dibenzo[b,d]thiophen-2-yl)butanoic acid (3). The reduced product (3) is then oxidized to the sulfone by six equivalents of m-chloroperoxybenzoic acid (mCPBA) in dichloromethane. Following the reaction, the solution is washed with basic water and purified by a normal phase column to afford the final product, 4-(5,5-dioxidodibenzo[b,d]thiophen-2-yl)butanoic acid (compound 4).

Scheme 1: Synthesis of compound 4

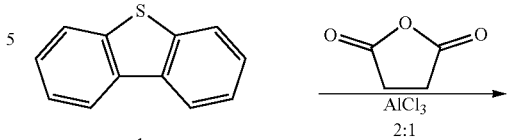

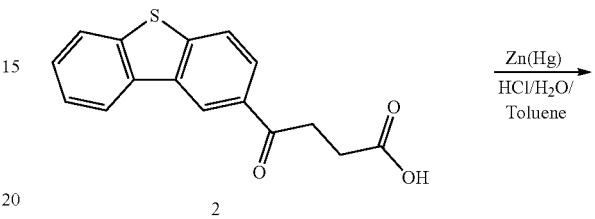

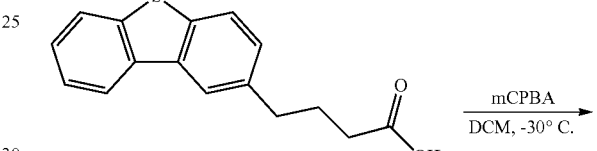

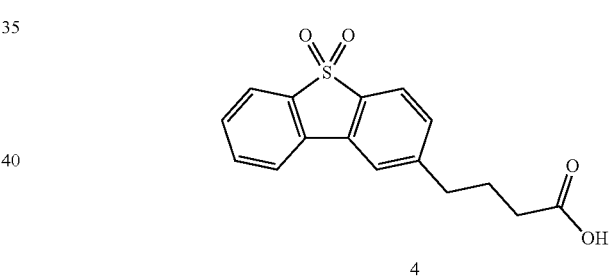

The synthesis of 4-(8-octyl-5,5-dioxidodibenzo[b,d]thiophen-2-yl)butanoic acid (Compound 9), which is a disubstituted dibenzothiophene-5,5-dioxide, is shown in Scheme 2. This molecule included an n-octyl substituent to potentially increase lipophilicity. The synthesis begins with a Grignard reaction with 2-bromodibenzothiophene (5) and octyl magnesium bromide in dry tetrahydrofuran (THF) with a catalyst. Following workup and purification with normal phase chromatography, 2-octyldibenzo[b,d]thiophene (6) is isolated in good yield (64%) and excellent purity as substantiated by clean 1H-NMR spectrum. The 2-octyldibenzo[b,d]thiophene (6) is then subjected to the same synthetic pathway that dibenzothiophene (1) is subjected to in preparing compound 4. As shown in Scheme 2, the addition of the oxobutanoic acid to form 4-(8-octyldibenzo[b,d]thiophen-2-yl)-4-oxobutanoic acid (7) is followed by reduction of the carbonyl to form 4-(8-octyldibenzo[b,d]thiophen-2-yl)butanoic acid (8). Finally, the oxidation of the sulfide to the sulfone afforded 4-(8-octyl-5,5-dioxidodibenzo[b,d]thiophen-2-yl)butanoic acid (compound 9) (Scheme 2).

Scheme 2: Synthesis of compound 9

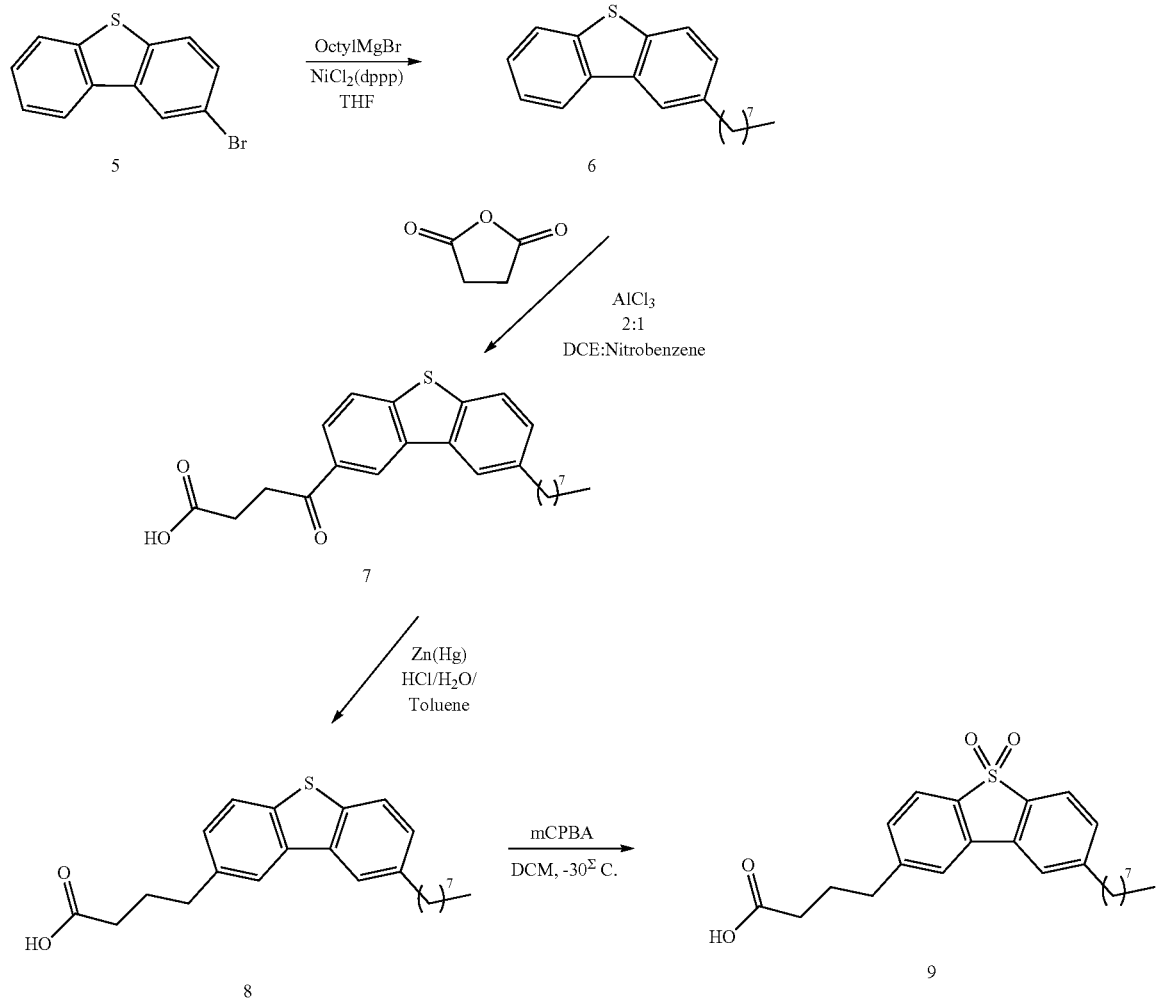

Some processes of the present invention include those for preparing a compound of Formula (II-a). These processes comprise reacting a compound having the structure of Formula (III) with a peroxy acid in the presence of a solvent to form the compound of Formula (II-a), wherein Formula (III) has the structure:

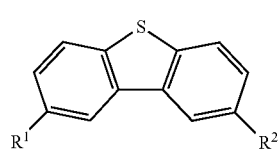

wherein $R^1$ and $R^2$ are as defined for Formula (II-a) above.

In various embodiments, the peroxy acid is m-chloroperoxybenzoic acid. Also, in some embodiments, the solvent comprises dichloromethane.

In further embodiments, the process further comprises reducing a compound of Formula (IV):

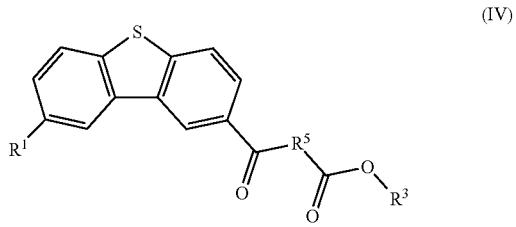

wherein $R^1$ and $R^3$ are as defined above for Formula (II-a) and $R^5$ is a bond, substituted or unsubstituted alkylene, substituted or unsubstituted alkenylene, or substituted or unsubstituted alkynylene.

In various embodiments, $R^5$ is substituted or unsubstituted $C_1$-$C_{20}$ alkylene, substituted or unsubstituted $C_2$-$C_{20}$ alkenylene, or substituted or unsubstituted $C_2$-$C_{20}$ alkynylene. In some embodiments, $R^5$ is a substituted or unsubstituted $C_1$-$C_{12}$ alkylene, substituted or unsubstituted $C_2$-$C_{12}$ alkenylene, or substituted or unsubstituted $C_2$-$C_{12}$ alkynylene. In certain embodiments, $R^5$ is $C_1$-$C_{12}$ alkylene, $C_2$-$C_{12}$ alkenylene, or $C_2$-$C_{12}$ alkynylene. In further embodiments, $R^5$ is $C_1$-$C_{12}$ alkylene, $C_4$-$C_{12}$ alkenylene, or $C_4$-$C_{12}$ alkynylene. In various embodiments, $R^5$ is a linear $C_1$-$C_6$ alkylene (e.g., a linear $C_2$ alkylene (ethylene)).

The reduction reaction can be conducted in the presence of a catalyst (e.g., zinc amalgam).

Various compounds of the present invention have been found to be efficient fluorescent dyes that can localize to the plasma membrane and/or cytoplasm of a cell. As such, the present invention is also directed to imaging agents comprising one or more compounds of Formula (I) (i.e., when n is 2) or Formula (II-a) as defined herein. The present invention is also directed to processes for visualizing a cell. Various processes of visualizing a cell typically comprise applying an imaging agent comprising one or more compounds of Formula (I) or (II-a) as defined herein to the cell, applying light to stimulate the emission of a luminescent signal from the imaging agent, and detecting the signal.

The imaging agents can be used to stain a cell for imaging using standard microscopy techniques measuring luminescence known in the art. In some embodiments, the imaging agents are applied to a living cell. In various embodiments, the imaging agents are applied to a fixed cell. In various embodiments the imaging agents are applied for a length of time (e.g., incubation time) to the cell. In further embodiments, the incubation time can be between 30 minutes to about 4 hours (e.g., about 3 hours).

Any imaging technique capable of detecting fluorescence known in the art may be used to detect the imaging agents. In some embodiments, cells can be imaged using microscopy using a luminescent probe (e.g., light) that excites the compounds described herein, resulting in the release of light of a certain wavelength that can then be detected. In various embodiments the emitted light is detected by a microscope and/or computer having imaging software. In some embodiments, confocal microscopy may be used. The luminescent probe can be a light having an excitation wavelength that maximally excites the compound, causing maximal luminescent emission. For example, the excitation wavelength can be between 200 and 300 nm, between 250 and 290 nm, or between 265 and 290 nm. In some embodiments, the excitation wavelength can be about 268 nm, about 274 nm, about 283 nm, or about 287 nm. In various embodiments, the excitation source is a laser.

When excited by the luminescent probe having the excitation wavelength described herein, the compounds comprising the imaging agent may emit light having an emission wavelength. The light having the emission wavelength can then be detected by a microscope and/or computer having imaging software calibrated to detect that wavelength. The compounds comprising the imaging agents described herein typically have an emission wavelength in the blue visible light range. Thus, the light having the emission wavelength can be detected visually through a microscope. The emission wavelength can range from about 350 nm to about 500 nm. In some embodiments, the emission wavelength can be between about 370 nm to about 495 nm. In certain embodiments, the emission wavelength can be about 371 nm, about 412 nm, about 421 nm, about 426 nm, about 485 nm, or about 492 nm.

The excitation and emission wavelengths chosen during a given imaging experiment should be optimized depending on experimental conditions. The experimental conditions are known to those skilled in the art and can include, but are not limited to, the solvents, media, temperature, and/or equipment (e.g., microscope, slides) chosen for the experiment. For example, the optimal excitation and emission wavelengths chosen for each compound can vary when the imaging agent is dissolved in ethanol compared to when it is dissolved in acetonitrile. The emission and excitation wavelengths described herein are meant to be illustrative and not limiting.

The compounds of the present invention have additional applications beyond the scope of microscopy. The sulfoxide analogs of formula (I) (i.e., where n is 1) and (II-b) can be irradiated with UV light (e.g., UVA, UVB, and UVC) to produce ground state atomic oxygen [$O(^3P)$], a reactive oxygen species (ROS). Recent findings suggest $O(^3P)$ may cause DNA cleavage, lipid oxidation, and initiate redox switching in proteins. Due to the similarity in DBTO and DBTOO properties, it is posited that the specific localization of the DBTOO dyes within a cell affords substantive evidence that the DBTO analog of the respective dye will localize in the same manner. The localization of photoactivatable $O(^3P)$-precursors is expected to open the door to more complex biological applications of $O(^3P)$.

Accordingly, the present invention further relates to methods of producing ground state atomic oxygen. In general, these methods comprise irradiating a sulfoxide analog of formula (I) (i.e., where n is 1) or (II-b) with UV light to produce ground state atomic oxygen [$O(^3P)$]. The sulfoxide analog can be applied to cells, tissues, or other living systems prior to irradiation.

Definitions

Unless otherwise indicated, the alkyl, alkenyl, alkynyl, and alkoxy groups described herein preferably containing from 1 to 30 carbon atoms in the principal chain. They can be straight chain (linear), branched chain, or cyclic. Also, unless otherwise indicated, the substituted alkyl, alkenyl, alkynyl, and alkoxy groups described herein can contain saturated or unsaturated and branched or unbranched carbon chains having from 1 to 20 carbon atoms in the principal chain.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl (e.g., cyano), substituted cycloalkyl and the like.

EXAMPLES

The following non-limiting examples are provided to further illustrate the present invention.

Methods and Materials

All chemicals were obtained from Alfa Aesar, Oakwood Chemical, Ark Pharm, ThermoFisher Scientific, and Sigma-Aldrich. They were used without further purification. Flash chromatography was performed using a Biotage Horizon with silica gel (SiliaFlash P60) purchased from SiliCycle. $^1H$ and $^{13}C$ NMR spectra were gathered on a Bruker DRX-400 in either DMSO-$d_6$ or CDCl$_3$. High-resolution mass spectra were measured using a ThermoScientific Q Exactive Orbitrap equipped with a Nano ESI ionization source. Absorption spectra were recorded using a Shimazdu UV-1800 UV-Vis spectrophotometer using samples contained in 10×10 mm quartz cell at a concentration of 0.01 mM. Fluorescence spectra were gathered on a Shuimazdu RF-5301 PC in a 10×10 mm quartz cuvette.

All images were captured with a Leica DM 400 B microscope with a DFC3000G camera (Leica Microsystems, Germany) and 63× oil immersion or 40× lenses. HeLa cells were staged according to the aforementioned methods. Leica LASX Core Software (Leica Microsystems, Germany) was used to acquire the images. All images were processed using ImageJ. The Pearson correlation coefficient was calculated using the image of a single cell using an ImageJ plugin called Colocalization Finder by Christophe Laummonerie and Jerome Mutterer of Institut de Biologie Moleculaire des Plantes.

HeLa cells were cultured in RPMI (ThermoFisher) supplemented with 10% FBS (ThermoFisher) and 1% penicillin-streptomycin (ThermoFisher 10000 U/mL). Cells (5000 cells/well in 100 μL) were plated in a 96-well culture plate (Greiner) and incubated for 120 h. Fifty microliters of the compound dissolved in complete media (final DMSO concentration 1%) at final concentrations of 100 μM, 10 μM, 1 μM, 100 nM, 10 nM, and 1 nM were added to the appropriate wells. After incubation of the cells at 37° C. in a humidified atmosphere of 5% $CO_2$ for 120 h, the cells were stained and incubated with MTS reagent (Promega) for 2 h to determine cell viability. The absorbance of each well was taken at 490 nm using a multimode plate reader (FlexStation 3, Molecular Devices, San Diego, Calif.). GraphPad Prism was used to analyze data to determine the percent viability. A two-way ANOVA was used to determine if the means of the compounds' effects on cell viability were significantly different from each other. Quadruplicate measurements were performed for each compound.

Example 1: Synthesis of 4-(5,5-dioxidodibenzo[b,d]thiophen-2-yl)butanoic Acid (4)

The general synthetic route to 4-(5,5-dioxidodibenzo[b,d]thiophen-2-yl)butanoic acid is shown in Scheme 1.

4-(dibenzo[b,d]thiophen-2-yl)-4-oxobutanoic Acid (2)

Dibenzothiophene (1) (1.008 g, 5.5 mmol) was combined with succinic anhydride (602 mg, 5.9 mmol) in a sealed two neck round bottom flask under nitrogen atmosphere. To the sealed flask, 7 ml of 2:1 dichloroethane (DCE)/nitrobenzene was injected by syringe. The mixture was stirred until a homogeneous solution was formed. The flask was then cooled to 0° C. by an ice water bath. Upon cooling, the $AlCl_3$ (1.494 g, 11.2 mmol) was added slowly to the stirring solution over several minutes. Once the $AlCl_3$ addition was complete, the solution was allowed to stir at room temperature for five hours. After the fifth hour of stirring at room temperature, the solution was warmed to 60° C. for 30 minutes. The solution was then allowed to cool to room temperature. It was then poured over HCl acidified water and washed with dichloromethane (DCM) 3×75 mL. The combined organic layers were dried with magnesium sulfate ($MgSO_4$) then the solution was evaporated under reduced pressure affording a dark brown oil. The oil was dissolved in minimal refluxing 2:1 ethyl acetate (EtOAc)/chloroform ($CHCl_3$) then placed in a freezer overnight. The resulting solid was recrystallized twice more using the same 2:1 EtOAc/$CHCl_3$ method before affording 733 mg of a slightly orange solid (47% yield) despite losing some on the benchtop. $^1$H NMR (400 MHz, CHLOROFORM-d) δ=8.80 (d, J=1.3 Hz, 1H), 8.29-8.23 (m, 1H), 8.09 (dd, J=1.7, 8.4 Hz, 1H), 7.94 (d, J=8.4 Hz, 1H), 7.91-7.86 (m, 1H), 7.57-7.49 (m, 2H), 3.52-3.42 (m, 2H), 2.94-2.86 (m, 2H) $^{13}$C NMR (CHLOROFORM-d, 101 MHz): δ (ppm) 197.4, 177.1, 144.9, 139.7, 135.7, 135.2, 133.0, 127.5, 125.9, 125.0, 123.0, 122.9, 121.9, 121.5, 33.4, 27.9

4-(dibenzo[b,d]thiophen-2-yl)butanoic Acid (3)

Zinc powder (2.15 g), mercuric chloride ($HgCl_2$) (225 mg), HCl (100 μL), and deionized (DI) water (2.75 ml) were combined in a 50 mL round bottom flask and stirred for five minutes. After the stirring, the liquid was decanted. To the flask with the remaining zinc amalgam, DI water (1.4 ml), HCl (325 μL), toluene (1.8 ml) and 2 (1.007 g, 3.5 mmol) were added. The solution was refluxed for 40 hours. During the reflux, approximately 300 μL of HCl was added every 6 hours during the day (3 additions). After reflux, the solution is poured over 30 ml of water acidified by 1.5 ml of HCl. The solution was washed with 3×50 mL DCM. The combined organic washes were dried with $MgSO_4$ and evaporated under reduced pressure with Celite. The resulting homogenous solid mixture was purified by normal phase flash chromatography using 1:1 EtOAc:hexanes with 0.1% acetic acid. The collected fractions were evaporated under reduced pressure to yield an off-white oil (567.2 mg, 58% yield) which eventually solidified.[24] $^1$H NMR (400 MHz, CHLOROFORM-d) δ=8.18-8.12 (m, 1H), 8.01-7.94 (m, 1H), 7.89-7.81 (m, 1H), 7.78 (d, J=8.2 Hz, 1H), 7.50-7.41 (m, 2H), 7.31 (dd, J=1.6, 8.2 Hz, 1H), 2.88 (t, J=7.6 Hz, 2H), 2.49-2.39 (m, 2H), 2.09 (quin, J=7.4 Hz, 2H) $^{13}$C NMR (CHLOROFORM-d, 101 MHz): δ (ppm) 177.1, 139.8, 137.6, 137.2, 135.8, 135.4, 127.6, 126.6, 124.3, 122.9, 122.7, 121.5, 121.3, 35.0, 32.8, 26.6

4-(5,5-dioxidodibenzo[b,d]thiophen-2-yl)butanoic Acid (4)

4-(dibenzo[b,d]thiophen-2-yl)butanoic acid (3) (86 mg, 0.3 mmol) was combined with 10 mL of DCM. To this solution, meta-Chloroperoxybenzoic acid (mCPBA) (77%) (279 mg, 1.6 mmol) was added. The solution was stirred overnight. After stirring, the solution was poured over 50 mL of saturated sodium bicarbonate water. An additional 20 mL of DCM was added. The organic layer was washed with 4×30 mL saturated sodium bicarbonate water. The organic layer was separated, dried with $MgSO_4$, and filtered. The dry organic layer was evaporated under reduced pressure with Celite. The resulting homogenous solid mixture was purified by normal phase flash chromatography using 1:1 EtOAc: hexanes with 0.1% acetic acid. The collected fractions were evaporated under reduced pressure to yield a white solid (63.8 mg, 66%). $^1$H NMR (400 MHz, DMSO-$d_6$) δ=12.10 (br. s., 1H), 8.20 (d, J=7.7 Hz, 1H), 8.06 (s, 1H), 7.95 (d, J=7.5 Hz, 1H), 7.88 (d, J=7.9 Hz, 1H), 7.80 (t, J=7.5 Hz, 1H), 7.65 (t, J=7.6 Hz, 1H), 7.48 (d, J=8.1 Hz, 1H), 2.76 (t, J=7.8 Hz, 2H), 2.27 (t, J=7.3 Hz, 2H), 1.90 (quin, J=7.6 Hz, 2H) $^{13}$C NMR (DMSO-$d_6$, 101 MHz): δ (ppm) 174.1, 149.2, 137.4, 134.7, 134.4, 131.2, 130.9, 130.9, 130.9, 122.6, 122.5, 121.9, 34.5, 33.0, 25.8 HRMS (ESI) calculated for $C_{16}H_{13}O_4S^-$ m/z: 301.0534, found m/z: 301.0540

Example 2: Synthesis of 4-(8-octyl-5,5-dioxidodibenzo[b,d]thiophen-2-yl)butanoic Acid (9)

The general synthetic route to 4-(8-octyl-5,5-dioxidodibenzo[b,d]thiophen-2-yl)butanoic acid is shown in Scheme 2.

2-octyldibenzo[b,d]thiophene (6)

To a three neck round bottom flask, 2-bromodibenzo[b,d]thiophene (5) (5.04 g, 19.2 mmol) and 1,3-Bis(diphenylphosphino)propane nickel(II) chloride [NiCl$_2$(dppp)] (517.0 mg, 0.9 mmol) were added. The flask was sealed and purged with nitrogen gas for 30 minutes. To the flask, and while remaining under a nitrogen atmosphere, 500 mL of dry tetrahydrofuran (THF) was added. The flask was then cooled to 0° C. with an ice water bath. Once cooled 12.3 mL (2.0 M) of octylmagnesium bromide (2M in ether) was slowly added by syringe. The solution was then stirred overnight at room temperature. Following the stirring, the solution was evaporated under reduced pressure with Celite. The resulting homogenous solid mixture was purified by flash chromatography using hexanes. The fractions associated with the product were evaporated under vacuum to afford a colorless oil (3.65 g, 64%). $^1$H NMR (DMSO-d$_6$, 400 MHz): δ (ppm) 8.31-8.37 (m, 1H), 8.18 (s, 1H), 7.96-8.03 (m, 1H), 7.90 (d, J=8.2 Hz, 1H), 7.45-7.54 (m, 2H), 7.36 (d, J=8.1 Hz, 1H), 2.76 (t, J=7.6 Hz, 2H), 1.67 (t, J=7.2 Hz, 2H), 1.15-1.39 (m, 10H), 0.79-0.89 (m, 3H) $^{13}$C NMR (DMSO-d$_6$, 101 MHz): δ (ppm) 139.2, 138.8, 135.8, 135.1, 135.0, 127.8, 126.9, 124.6, 123.0, 122.7, 121.9, 121.4, 35.1, 31.3, 31.2, 28.8, 28.7, 28.6, 22.1, 13.9

4-(8-octyldibenzo[b,d]thiophen-2-yl)-4-oxobutanoic Acid (7)

2-octyldibenzo[b,d]thiophene (6) (2 g, 6.7 mmol) and succinic anhydride (742 mg, 7.3 mmol) were added to a round bottom flask, sealed with a rubber stopper, and placed under a continuous flow of nitrogen gas. To the sealed flask, 14 mL of 2:1 dichloroethane (DCE)/nitrobenzene was injected by syringe. The mixture was stirred until a homogenous solution formed. The flask was then cooled to 0° C. by an ice water bath. Upon cooling, the AlCl$_3$ (1.8 g, 13.4 mmol) was added slowly to the stirring solution over several minutes. Once the AlCl$_3$ addition was complete, the solution was allowed to stir at room temperature for five hours. After the fifth hour of room temperature stirring, the solution was warmed to 60° C. for 30 minutes. The solution was then allowed to cool to room temperature, when it was then poured over HCl acidified water and washed with dichloromethane (DCM) 3×75 ml. The combined organic layers were dried with magnesium sulfate (MgSO$_4$), then the solution was evaporated under reduced pressure affording a dark oil. The oil was dissolved in minimal refluxing 2:1 ethyl acetate (EtOAc):chloroform (CHCl$_3$) then placed in a freezer overnight. The resulting solid was recrystallized twice more using the same 2:1 EtOAc/CHCl$_3$ method before affording an off-white solid (705 mg, 26%). $^1$H NMR (DMSO-d6, 400 MHz): δ (ppm) 12.17 (s, 1H), 9.02 (s, 1H), 8.43 (s, 1H), 8.15 (d, J=8.4 Hz, 1H), 8.05 (d, J=8.4 Hz, 1H), 7.96 (d, J=8.1 Hz, 1H), 7.42 (d, J=8.2 Hz, 1H), 3.45 (t, J=6.2 Hz, 2H), 2.78 (t, J=7.6 Hz, 2H), 2.61-2.69 (m, 2H), 1.64-1.77 (m, 2H), 1.33 (br. s., 2H), 1.16-1.30 (m, 10H), 0.84 (t, J=6.5 Hz, 3H) $^{13}$C NMR (DMSO-d6, 101 MHz): δ (ppm) 198.2, 173.9, 143.9, 139.7, 136.2, 135.1, 135.0, 133.3, 128.4, 125.6, 123.2, 122.8, 122.1, 122.0, 35.1, 33.3, 31.3, 31.3, 28.8, 28.7, 28.7, 28.0, 22.1, 13.9 MS (ESI) calculated for C$_{24}$H$_{27}$O$_3$S$^-$ m/z: 395.168, found m/z: 395.1687

4-(8-octyldibenzo[13,d]thiophen-2-yl)butanoic Acid (8)

Zinc powder (310 mg), mercuric chloride (HgCl$_2$) (33 mg), HCl (15 μl), and DI water (360 μl) were combined in a 50 ml round bottom flask and stirred for five minutes. After the stirring, the liquid was decanted. To the flask with the remaining zinc amalgam, DI water (200 μl), HCl (33 μl), toluene (250 μl) and 7 (202 mg, 0.5 mmol) were added. The solution was refluxed for 40 hours. During the reflux, approximately 50 μl of HCl was added every 6 hours during the day (3 additions). After reflux, the solution is poured over 30 ml of water acidified by 1.5 ml of HCl. The solution was washed with 3×25 ml DCM. The combined organic washes were dried with MgSO$_4$ and evaporated under reduced pressure with Celite. The resulting homogenous solid mixture was purified by normal phase flash chromatography using 15% EtOAc and 85% hexanes with 0.1% acetic acid which elutes byproducts then 65% EtOAc and 35% hexanes with 0.1% acetic acid. The fractions associated with the product were evaporated under reduced pressure to yield an off-white oil (147 mg, 76%) which eventually solidifies. $^1$H NMR (CHLOROFORM-d, 400 MHz): δ (ppm) 7.94-7.97 (m, 2H), 7.75 (t, J=7.9 Hz, 2H), 7.29 (d, J=8.3 Hz, 2H), 2.87 (t, J=7.6 Hz, 2H), 2.75-2.81 (m, 2H), 2.46 (s, 2H), 2.04-2.13 (m, 2H), 1.67-1.76 (m, 2H), 1.22-1.44 (m, 10H), 0.86-0.92 (m, 3H) $^{13}$C NMR (DMSO-d6, 101 MHz): δ (ppm) 174.3, 139.0, 138.2, 136.4, 136.1, 135.2, 135.1, 127.7, 127.6, 122.8, 122.6, 121.4, 121.4, 35.1, 34.4, 33.1, 31.3 MS (ESI) calculated for C$_{24}$H$_{29}$O$_2$S$^-$ m/z: 381.188, found m/z: 381.1895

4-(8-octyl-5,5-dioxidodibenzo[13,d]thiophen-2-yl)butanoic Acid (9)

4-(8-octyldibenzo[b,d]thiophen-2-yl)butanoic acid (8) (108 mg, 0.28 mmol) was combined with 10 ml of DCM. To this solution meta-Chloroperoxybenzoic acid (mCPBA) (77%) (292 mg, 1.7 mmol) was added. The solution was stirred overnight for convenience. After stirring the solution was poured over 50 ml of saturated sodium bicarbonate water. An additional 20 ml of DCM was added. The organic layer was washed with 4×30 ml saturated sodium bicarbonate water. The organic layer was separated, dried with MgSO$_4$, and filtered. The dried solution was then purified on four separate preparative thin layer chromatography plates using 1:1 EtOAc: hexanes with 0.1% acetic acid. The silica bands associated with the product were collected and then filtered with EtOAc with 3% methanol. The filtrate was evaporated under vacuum to afford a white solid (103 mg, 92%). $^1$H NMR (400 MHz, CHLOROFORM-d) δ=8.01-7.92 (m, 2H), 7.75 (t, J=7.8 Hz, 2H), 7.30 (s, 2H), 2.87 (t, J=7.6 Hz, 2H), 2.83-2.74 (m, 2H), 2.44 (t, J=7.4 Hz, 2H), 2.11-2.06 (m, 2H), 1.72 (quin, J=7.4 Hz, 2H), 1.44-1.26 (m, 10H), 0.93-0.84 (m, 3H) $^{13}$C NMR (DMSO-d6, 101 MHz): δ (ppm) 174.1, 149.8, 149.0, 135.2, 135.0, 131.3, 131.2, 130.7, 130.7, 122.4, 121.8, 121.7, 35.2, 34.5, 33.0, 31.2, 30.5, 28.7, 28.6, 25.8, 22.0, 13.9 MS (ESI) calculated for C$_{24}$H$_{29}$O$_4$S$^-$ m/z: 413.178, found m/z: 413.1794

Example 3: Fluorescence Imaging

Figure 5:
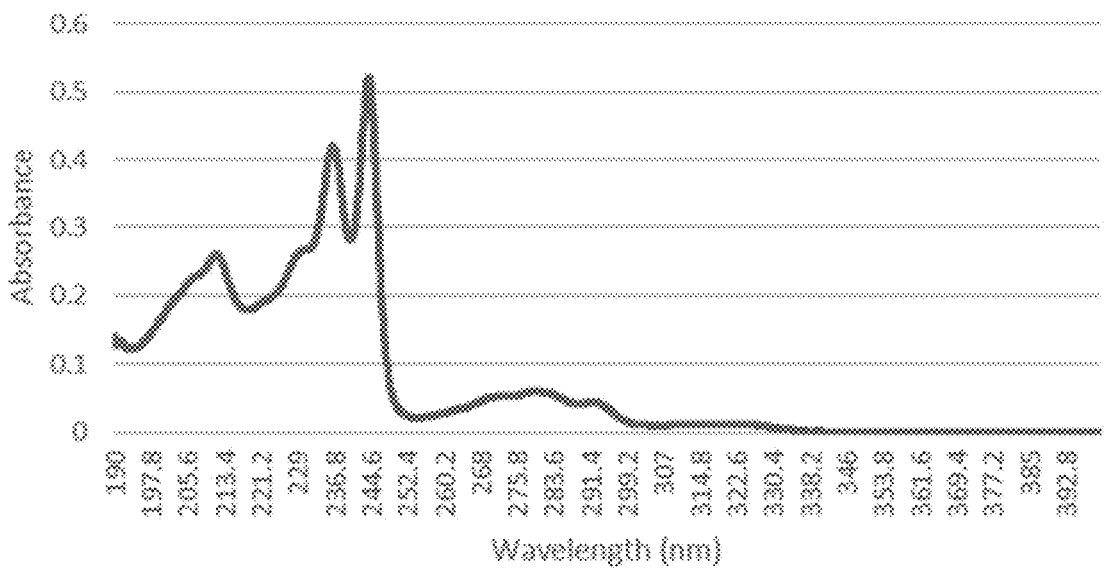
FIG. 5 presents graphs of UV/visible light absorbance of compounds 4 and 9.
Figure 5:
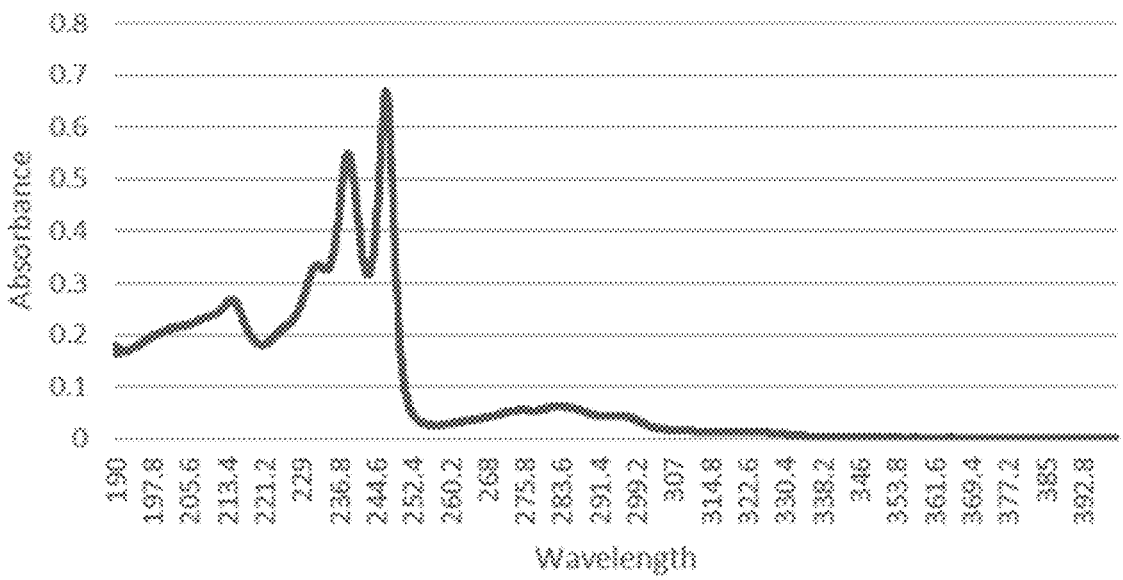

The two dyes, upon their successful synthesis and isolation, had their photophysical data gathered beginning with absorbance, which was measured through the visible and ultraviolet region. Absorbance spectra were gathered using 0.01 mM solutions of the respective compound in HPLC grade acetonitrile. The spectra are nearly identical. See FIG. 5. This was of no surprise as the chromophore is the same on both molecules; however, 9 has a more substantial absorbance than 4 with a respective molar absorptivity of 66,000 M$^{-1}$cm$^{-1}$ and 51,700 M$^{-1}$ cm$^{-1}$. The absorbance determination was followed by the fluorescence emission and excitation spectra being gathered using solutions where the absorbance of the respective compound was 0.041 at 250 nm in acetonitrile (FIG. 1). This was done to save material as the same solutions were then used to determine the fluorescent quantum yield. The excitation spectra of 4 and 9 followed the same pattern, though the two were slightly offset from one another when overlaid with respect to the x-axis.

The emission spectra of 4 and 9 are all but identical, peaking at 359 nm and 357 nm, respectively. Both emission spectra display a broad undefined shape with no resolved vibronic features, which was also seen with the first series of DBTOO fluorescent stains (5). There have been extensive studies of DBT. DBTO and DBTOO derivatives with the majority displaying no long lifetime luminescence in solution. In one exception, 2,8-disubstitution of DBTOO with phenothiazines, which act as donor moieties, produce a donor-acceptor relationship that lead to a longlifetime emission in solution. The significant Stokes shift observed for 4 and 9 can suggest a contribution from longer lifetime luminescence event. However, the luminescence intensity only decreased 20% when a degassed sample was exposed to air. Since oxygen can completely quench luminescence involving triplet states, this result suggested the observed luminescence arises from prompt fluorescence though a contribution from delayed fluorescence or phosphorescence cannot be conclusively excluded.

The fluorescent quantum yield was then determined by the single point method with Eq. 1.

$$Q = Q_R \frac{I}{I_R} \frac{OD_R}{OD} \frac{N^2}{N_R^2} \qquad \text{Equation 1}$$

Naphthalene was used as the standard where it was also made into a solution with acetonitrile at a concentration which allowed the absorbance to be 0.041 at 250 nm. The fluorescent quantum yields of 4 and 9 were determined to be 0.40 and 0.67, respectively.

TABLE 1

Photophysical data for 4 and 9

| Compd. | $\lambda_{abs}$ (nm)[a, b] | $\lambda_{ex}$ (nm)[a, c] | $\lambda_{em}$ (nm)[a, d] | Stokes Shift (nm) | log $\varepsilon_{max}$ (M$^{-1}$ cm$^{-1}$)[e] | $\varphi^{a, f}$ |
|---|---|---|---|---|---|---|
| 4 | 244 | 244 | 359 | 38 | 3.71 | 0.4 |
| 9 | 247 | 248 | 357 | 38 | 3.81 | 0.67 |

[a]Measured in CAN;
[b]Absorbance maxima;
[c]Excitation maxima;
[d]Emission maxima;
[e]Maximum molar extinction coefficient;
[f]Fluorescent quantum yield measured by the single point method Fluorescence Imaging without Co-Stain The dyes, having displayed efficient fluorescence in the visible region, were then imaged using fluorescent microscopy with HeLa cells. The chosen method was used initially to verify if 4 and 9 were viable dyes.

Sterile glass poly-D-lysine coated #1.5 cover slips (NeuVitro), pre-incubated with culture medium, were placed in sterile 6-well plates. A single cell suspension of the HeLa (cervical cancer cell) cell line was prepared at $5 \times 10^4$ cells mL$^{-1}$ in the appropriate medium. Volumes of 2.0 mL were pipetted into each of the wells containing the coverslips. The 6-well plate was left overnight at 37.0° C. in a 5.0% CO$_2$ incubator. Following the overnight incubation, the plate was aspirated dry and then PBS, containing the drug (at 5.0 uM and 0.10% DMSO) in a volume of 2.0 mL, was gently pipetted onto the cell monolayers attached to the glass cover slips. Cells on the cover slips were exposed to the dye for approximately 2 hours in the incubator at 37.0° C. in a 5.0% CO$_2$. Cells were washed with PBS and treated with 4.0% paraformaldehyde solution prepared in PBS, incubated for 30 minutes at room temperature for full fixation. Three washes with 1 ml of PBS were completed to ensure excess solution was rinsed away. Glass cover slips were removed and mounted on slides with ProLong Gold Antifade Mountant (ThermoFisher Scientific). The specimen was dried for several minutes and sealed with clear nail polish before visualized under a Leica microscope.

Figure 2:
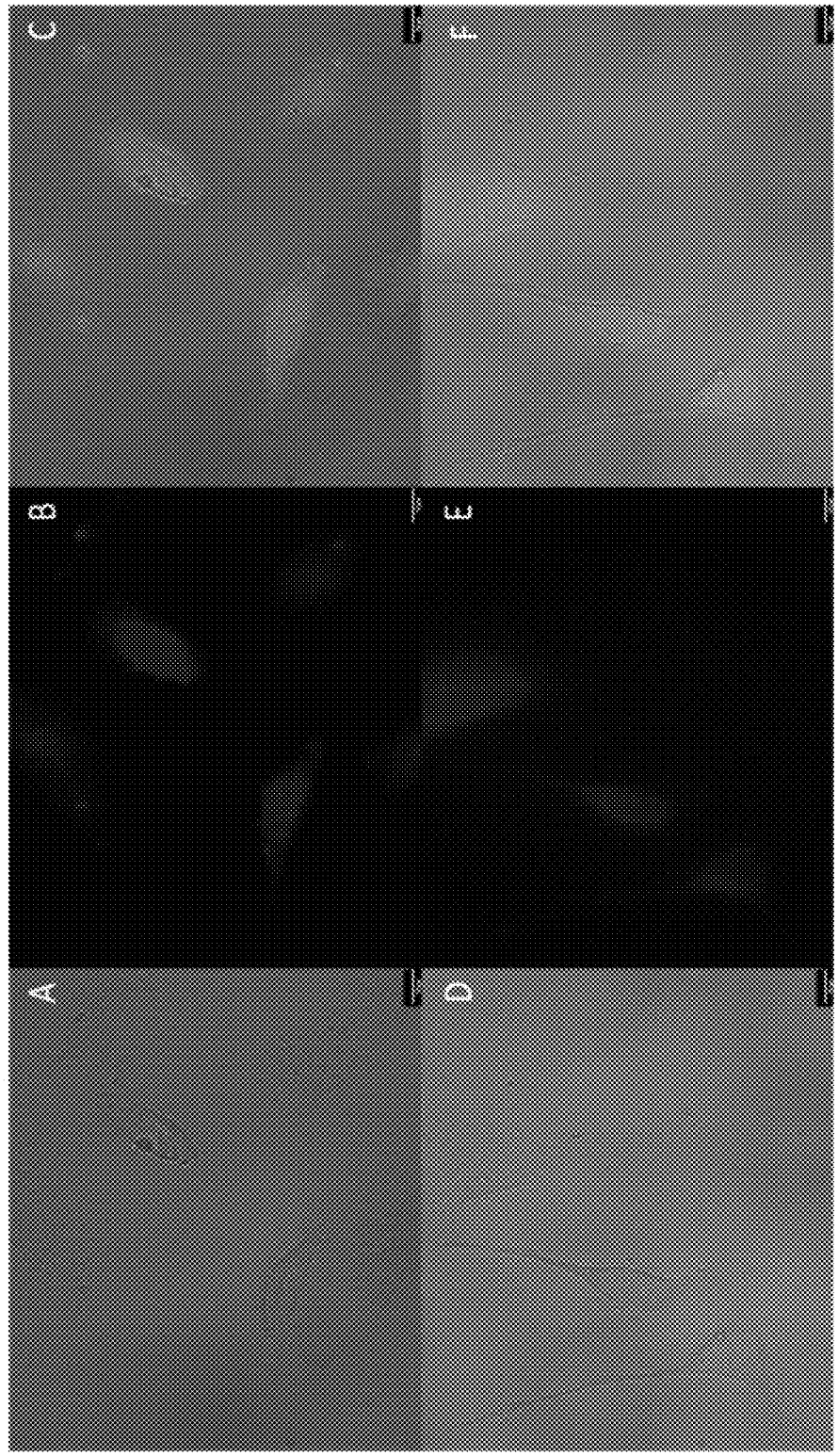
FIG. 2 presents fluorescence images of HeLa cells stained using compounds 4 and 9: (A) Bright-field image of cells stained with compound 4. (B) Fluorescence image of HeLa cells stained with compound 4. (C) Merged bright-field and fluorescence images of HeLa cells stained with compound 4. (D) Bright-field image of cells stained with compound 9. (E) Fluorescence image of HeLa cells stained with compound 9. (F) Merged bright-field and fluorescence images of HeLa cells stained with compound 9.

The replication of the previously reported method afforded good images (FIG. 2). The diffuse emission of the dyes about the entirety of the cell suggests either cytoplasm or plasma membrane localization. This initial round of imaging was done without a co-stain, and thus a conclusion could not be made. The smaller dye, 4, which is seen in frames A, B, and C has a stronger emission from the center of the cell, allowing the possibility that subcellular organelle membranes may also be penetrated by the dye. The octyl functionalized dye, 9, possess a more extranuclear emission indicating that more superficial areas are targeted by this dye as seen in frames D, E, and F of FIG. 2. While few absolutes were yielded from this imaging, these results show the dyes as functional fluorescent stains and, more importantly, demonstrates that these dyes may be used for incubation times of up to 2 hours and potentially more.

Fluorescence Imaging with Co-Stain

To further optimize staining and understand the localization of the dyes in HeLa cells, a co-stain was introduced to the cells with the dyes while also utilizing a shorter incubation time. Sterile glass poly-D-lysine coated #1.5 cover slips (NeuVitro), pre-incubated with culture medium, were placed in sterile 6-well plates. A single cell suspension of the HeLa (cervical cancer cells) cell line was prepared at $5 \times 104$ cells ml-1 in the appropriate medium. Volumes of 2.0 mL were pipetted into each of the wells containing the coverslips. The 6-well plate was left overnight at 37.0° C. in a 5.0% CO$_2$ incubator. Following the overnight incubation, the plate was aspirated and PBS, containing the CellMask Orange (ThermoFischer Scientific) (at 1000× dilution with 0.10% DMSO) in a volume of 1.8 mL, was gently pipetted onto the cell monolayers attached to the glass cover slips. To the CellMask doped PBS 200 µl of 4 or 9 at 50 µM was added to the respective well. Cells on the cover slips were exposed to the dye for approximately 10 minutes. Cells were washed with PBS and treated with 4.0% paraformaldehyde solution prepared in PBS, incubated for 30 minutes at room temperature for full fixation. Three washes with 1 ml of PBS were completed to ensure excess solution was rinsed away. Glass cover slips were removed and mounted on slides with ProLong Gold Antifade Mountant (ThermoFisher Scientific) . The specimen was dried for several minutes and sealed with clear nail polish before visualized under a microscope.

Figure 3:
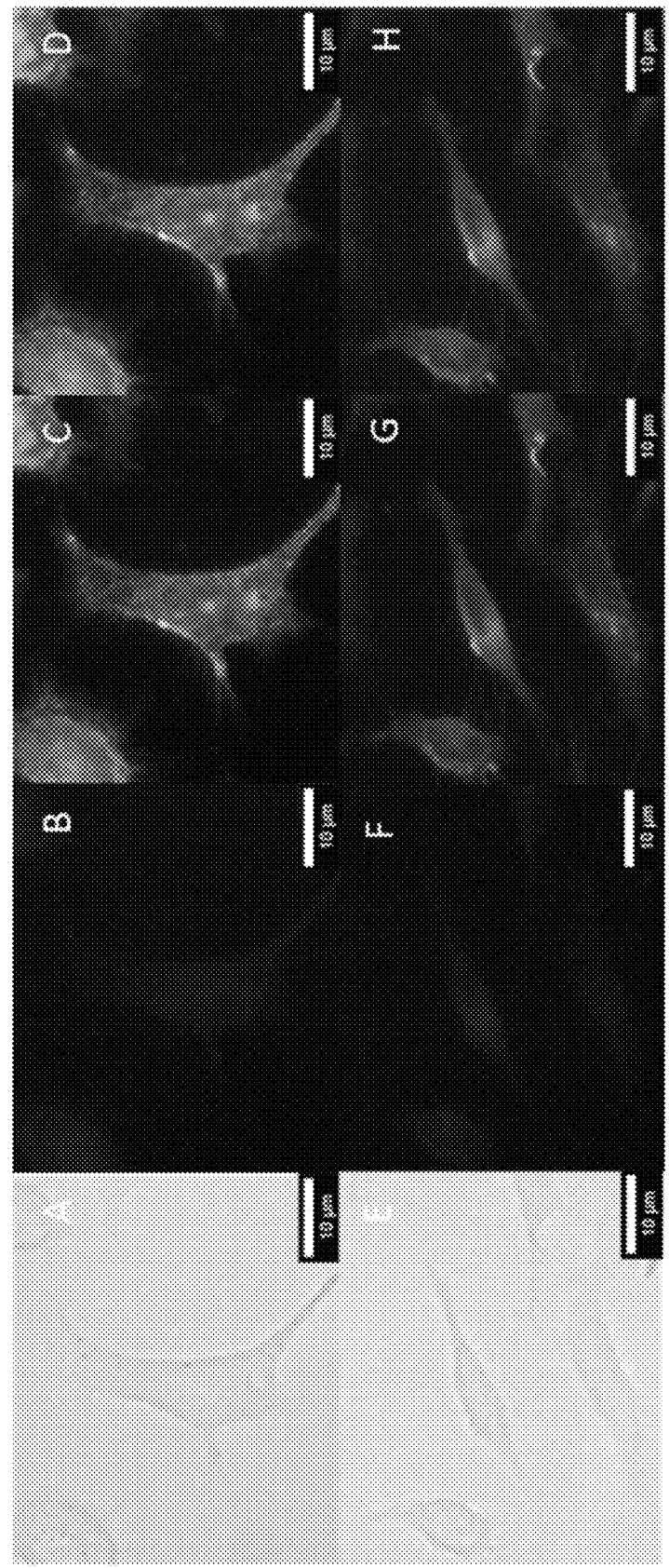
FIG. 3 presents a brightfield and fluorescence images of HeLa cells stained using compounds 4 and 9 and co-stained with CellMask Orange: (A) Bright-field image of cells stained with compound 4. (B) Fluorescence (DAPI) image of HeLa cells stained with compound 4 and CellMask Orange. (C) Fluorescence (Cy-5) image of HeLa cells stained with compound 4 and CellMask Orange (D) Merged images of the DAPI and Cy-5 images from staining with compound 4 and CellMask Orange. (E) Bright-field image of cells stained with compound 9. (F) Fluorescence (DAPI) image of HeLa cells stained with compound 9 and CellMask Orange. (G) Fluorescence (Cy-5) image of HeLa cells stained with compound 9 and CellMask Orange (H) Merged images of the DAPI and Cy-5 images from staining with compound 9 and CellMask Orange.

The modest modification came in two parts; the PBS used to replace the media was now doped with a 1000× dilution of CellMask Orange (plasma membrane dye) and the incubation time for the co-stain and dyes was shortened to 10 minutes. These subtle modifications were done to determine if the dyes, 4 and 9, could be used with short incubation periods and to follow the manufacture's staining instructions for CellMask Orange. The changes indicated that 4 and 9 localize in the plasma membrane. CellMask Orange is a known dye which readily localizes in the plasma membrane. It also does not absorb below 400 nm thus the DAPI filter set used to image 4 and 9 would not excite the CellMask Orange. The co-stained HeLa cells were imaged by brightfield and fluorescent techniques where 4 and 9 were viewed through the DAPI filter set and the CellMask Orange was imaged by a Cy-5 filter set. See FIG. 3. As seen in frames D and H, both 4 and 9 overlap well with the respective images taken of CellMask Orange. The overlap was quantified using a Pearson correlation coefficient calculation with the Colocalization Finder plugin for ImageJ using a single cell image cropped from the images. The Pearson correlation coefficient for 4 and 9 with the CellMask Orange were 0.66 and 0.81, respectively, which are reasonably strong values affording quantifiable evidence that 4 and 9 localize in the plasma membrane. The lower value for 4 may be rationalized by referencing the earlier set of images where the dye likely penetrated intracellular membranes. Keeping this possibility in mind, it is noted that CellMask Orange does not penetrate well into subcellular membranes with a short incubation time. Minding those two points affords a reasonable conclusion as to why 4 has a lower Pearson correlation coefficient compared to 9. The more substantial overlap quantified with regards to 9 may come as a function the large octyl tail it possesses, which may prevent the dye from readily accessing intracellular domains. Maintaining 9 primarily in the plasma membrane mimics the effect of CellMask Orange more closely.

Figure 4:
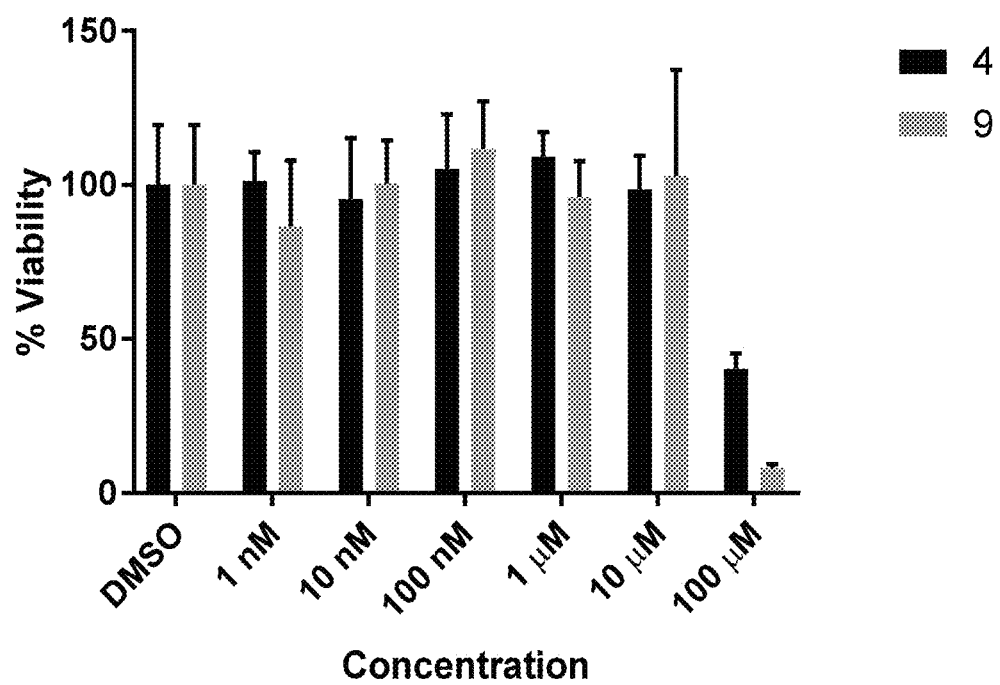
FIG. 4 presents a graph showing the results of a metabolic proliferation assay with HeLa cells, 120 h incubation, n=4.

Having verified the capacity of 4 and 9 to fluoresce well in cells and localize in the plasma membrane with a reasonably strong exclusivity, the toxicity of the compounds was determined. The toxicity of 4 and 9 was determined in HeLa cells. The HeLa cells were treated with concentrations of the respective dye varying between 1 nm and 100 µM for 72 hours. As seen in FIG. 4, neither dye displayed toxicity at concentrations, which would be needed for application by standard imaging protocols; while they do display toxicity at 100 µM, it is not so concerning to most microscopy related situations.

CONCLUSION

Two new plasma membrane dyes were designed and synthesized. These dyes displayed efficient fluorescence with fluorescent quantum yields and a meaningful portion of their respective emission extending into the visible region despite peaking in the UV region, and thus, they are well visible to both the eye and camera. The photophysics of 4 and 9 was agreeable with the DAPI filter set of a fluorescent microscope, and good images were gathered during both short and long incubation times. Co-staining with CellMask Orange demonstrated that the dyes localized in the plasma membranes, and in the case of 4, this may extend into intracellular membranes. Both dyes possessed reasonable strong Pearson correlation coefficients quantitatively verifying they overlapped well with the CellMask Orange which stains the plasma membrane. Thus, this works shows that DBTOO fluorophores, given the appropriate functionalization, are applicable tools in fluorescent microscopy.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions, products, and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

REFERENCES (1) Wiederschain, G. Y. Biochemistry (Moscow) 2011, 76, 1276.
(2) Specht, E. A.; Braselmann, E.; Palmer, A. E. Annual Review of Physiology 2017, 79, 93.
(3) Lavis, L. D.; Raines, R. T. ACS Chemical Biology 2008, 3, 142.
(4) Terai, T.; Nagano, T. Pflügers Archiv—European Journal of Physiology 2013, 465, 347.
(5) Petroff II, J. T.; Skubic, K. N.; Arnatt, C. K.; McCulla, R. D. J Org Chem 2018, 83, 14063.
(6) Lucien, E.; Greer, A. The Journal of Organic Chemistry 2001, 66, 4576.
(7) Thomas, K. B.; Greer, A. The Journal of Organic Chemistry 2003, 68, 1886.
(8) Bucher, G.; Scaiano, J. C. The Journal of Physical Chemistry 1994, 98, 12471.
(9) Cubbage, J. W.; Tetzlaff, T. A.; Groundwater, H.; McCulla, R. D.; Nag, M.; Jenks, W. S. The Journal of Organic Chemistry 2001, 66, 8621.
(10) Gregory, D. D.; Wan, Z.; Jenks, W. S. Journal of the American Chemical Society 1997, 119, 94.
(11) McCulla, R. D., Iowa State University, 2005.
(12) McCulla, R. D.; Jenks, W. S. Journal of the American Chemical Society 2004, 126, 16058.
(13) Nag, M.; Jenks, W. S. The Journal of Organic Chemistry 2004, 69, 8177.
(14) Stoffregen, S. A.; Lee, S. Y.; Dickerson, P.; Jenks, W. S. Photochemical & Photobiological Sciences 2014, 13, 431.
(15) Vos, B. W.; Jenks, W. S. Journal of the American Chemical Society 2002, 124, 2544.
(16) Wan, Z.; Jenks, W. S. Journal of the American Chemical Society 1995, 117, 2667.
(17) WAUCHOPE, 0. R.; SHAKYA, S.; SAWWAN, N.; LIEBMAN, J. F.; GREER, A. Journal of Sulfur Chemistry 2007, 28, 7.
(18) Bourdillon, M. T.; Ford, B. A.; Knulty, A. T.; Gray, C. N.; Zhang, M.; Ford, D. A.; McCulla, R. D. Photochemistry and Photobiology 2014, 90, 386.
(19) Korang, J., Saint Louis University, 2012.
(20) Korang, J.; Emahi, I.; Grither, W. R.; Baumann, S. M.; Baum, D. A.; McCulla, R. D. RSC Advances 2013, 3, 12390.
(21) Korang, J.; Grither, W. R.; McCulla, R. D. Journal of the American Chemical Society 2010, 132, 4466.
(22) Omlid, S. M.; Zhang, M.; Isor, A.; McCulla, R. D. The Journal of Organic Chemistry 2017.

(23) Zhang, M.; Ravilious, G. E.; Hicks, L. M.; Jez, J. M.; McCulla, R. D. Journal of the American Chemical Society 2012, 134, 16979.
(24) Sidorenko Neftekhimiya 1984, 24, 3.
(25) Liu, J.; Hu, S.; Zhao, W.; Zou, Q.; Luo, W.; Yang, W.; Peng, J.; Cao, Y. Macromolecular Rapid Communications 2010, 31, 496.
(26) Turro, N. J. Modern Moelcular Photochemistry; University Science Books: United State of America, 1991.
(27) Jenks, W. S.; Lee, W.; Shutters, D. The Journal of Physical Chemistry 1994, 98, 2282.
(28) Rockafellow, E. M.; McCulla, R. D.; Jenks, W. S. Journal of Photochemistry and Photobiology A: Chemistry 2008, 198, 45.
(29) B., D. F.; Jose, S.; R., G. D.; Przemyslaw, D.; S., N. R.; A., F. M.; S., B. A.; Tiago, P.; N., B.-S. M.; R., B. M.; P., M. A. Advanced Science 2016, 3, 1600080.
(30) Lakowicz, J. R. Principles of Fluorescence Spectroscopy; Springer US, 2007.
(31) Dunn, K. W.; Kamocka, M. M.; McDonald, J. H. American Journal of Physiology-Cell Physiology 2011, 300, $C_{723}$.
(32) Renz, M. Cytometry Part A 2013, 83, 767.

What is claimed is:

1. A compound of Formula (I), or salt thereof:

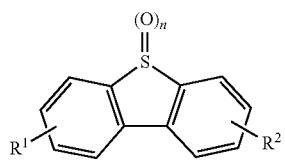

wherein
R$^1$ is hydrogen, hydroxy, substituted or unsubstituted hydrocarbyl, or substituted or unsubstituted amino;
R$^2$ is:

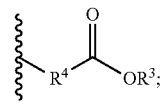

R$^3$ is hydrogen, substituted or unsubstituted alkyl; or substituted or unsubstituted alkenyl;
R$^4$ is unsubstituted $C_1$-$C_3$ alkylene or substituted or unsubstituted alkenylene; and
n is 1 or 2.

2. The compound of claim 1, wherein R$^1$ is unsubstituted $C_1$-$C_{20}$ alkyl or unsubstituted $C_2$-$C_{20}$ alkenyl, substituted or unsubstituted $C_1$-$C_{20}$ alkoxy, substituted or unsubstituted aryl, or substituted or unsubstituted heteroaryl.

3. The compound of claim 1, wherein R$^1$ is substituted or-unsubstituted $C_1$-$C_{12}$ alkyl, substituted or unsubstituted $C_2$-$C_{12}$ alkenyl, substituted or unsubstituted $C_1$-$C_{12}$ alkoxy, substituted or unsubstituted phenyl, substituted or unsubstituted biphenyl, substituted or unsubstituted naphthyl, or substituted or unsubstituted anthracenyl.

4. The compound of claim 1, wherein R$^1$ is a linear or branched $C_1$-$C_{12}$ alkyl.

5. The compound of claim 1, wherein R$^3$ is hydrogen, substituted or unsubstituted $C_1$-$C_{20}$ alkyl or substituted or unsubstituted $C_2$-$C_{20}$ alkenyl.

6. The compound of claim 1, wherein R$^3$ is hydrogen, $C_1$-$C_{12}$ alkyl, $C_2$-$C_{12}$ alkenyl, or $C_2$-$C_{12}$ alkynyl.

7. The compound of claim 1, wherein R$^3$ is hydrogen.

8. The compound of claim 1, wherein R$^4$ is a unsubstituted $C_3$ alkylene or unsubstituted $C_2$-$C_{12}$ alkenylene.

9. The compound of claim 1, wherein R$^4$ is a $C_3$ alkylene.

10. The compound of claim 1, wherein R$^1$ and R$^2$ are different.

11. The compound of claim 1, wherein the compound has a structure of formula (II-a):

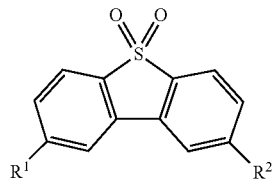

wherein R$^1$ and R$^2$ are as defined for Formula (I) above.

12. A compound having a structure selected from the group consisting of:

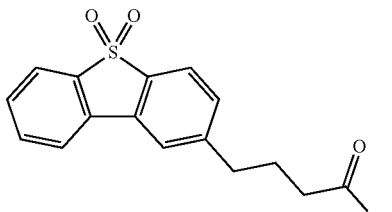

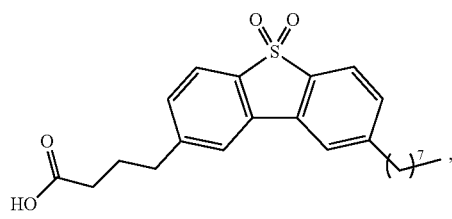

and salts thereof.

13. A compound having a structure of formula (II-b):

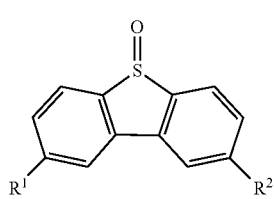

wherein
R¹ is hydrogen, hydroxy, substituted or unsubstituted hydrocarbyl, or substituted or unsubstituted amino;
R² is:

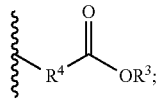

R³ is hydrogen, substituted or unsubstituted alkyl, substituted or unsubstituted alkenyl, or substituted or unsubstituted alkynyl;
R⁴ is substituted or unsubstituted alkylene, substituted or unsubstituted alkenylene, or substituted or unsubstituted alkynylene; and
n is 1 or 2.

14. A process of visualizing a cell comprising applying an imaging agent comprising a compound of Formula (I), or salt thereof to the cell, applying light to stimulate the emission of a luminescent signal from the imaging agent, and detecting the signal, wherein the compound of Formula (I), or salt thereof has a structure corresponding to:

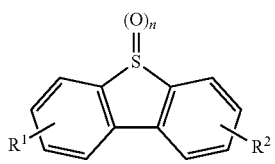 (I)

wherein
R¹ is hydrogen, hydroxy, substituted or unsubstituted hydrocarbyl, or substituted or unsubstituted amino;
R² is:

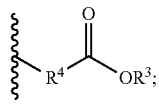

R³ is hydrogen, substituted or unsubstituted alkyl, substituted or unsubstituted alkenyl, or substituted or unsubstituted alkynyl;
R⁴ is substituted or unsubstituted alkylene, substituted or unsubstituted alkenylene, or substituted or unsubstituted alkynylene; and
n is 1 or 2.

15. A method of producing ground state atomic oxygen, the method comprising irradiating a compound of claim 13 with UV light to produce ground state atomic oxygen [O(³P)].

16. The method of claim 15, further comprising applying the compound to a cell, tissue, or other living system prior to irradiation.

17. A process for preparing a compound of claim 11, the process comprising reacting a compound having the structure of Formula (III) with a peroxy acid in the presence of a solvent to form the compound of Formula (II-a), wherein Formula (III) has the structure:

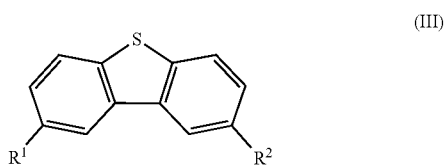 (III)

wherein R¹ and R² are as defined for Formula (II-a) above.

18. An imaging agent comprising one or more of the compounds of claim 1.

19. The method of claim 14, wherein the compound of Formula (I) has a structure selected from the group consisting of:

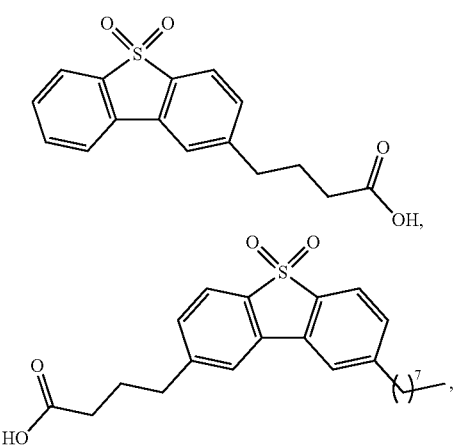

and salts thereof.

* * * * *